(12) United States Patent
Shieh et al.

(10) Patent No.: US 12,186,429 B2
(45) Date of Patent: Jan. 7, 2025

(54) EXOSOME AND PREPARATION PROCESS AND USE THEREOF

(71) Applicant: Ascension Medical Biotechnology Co., Ltd., Taipei (TW)

(72) Inventors: Ju-Sheng Shieh, Taipei (TW); Yu-Tang Chin, Taipei (TW)

(73) Assignee: Ascension Medical Biotechnology Co., Ltd., Taipei (TW)

( * ) Notice: Subject to any disclaimer, the term of this patent is extended or adjusted under 35 U.S.C. 154(b) by 129 days.

(21) Appl. No.: 17/849,389

(22) Filed: Jun. 24, 2022

(65) Prior Publication Data

US 2023/0255887 A1 Aug. 17, 2023

(30) Foreign Application Priority Data

Feb. 14, 2022 (TW) .................................. 111105325

(51) Int. Cl.
| | | |
|---|---|---|
| *A61K 9/127* | (2006.01) | |
| *A61K 8/14* | (2006.01) | |
| *A61P 17/02* | (2006.01) | |
| *A61Q 19/08* | (2006.01) | |

(52) U.S. Cl.
CPC ................ *A61K 9/127* (2013.01); *A61K 8/14* (2013.01); *A61P 17/02* (2018.01); *A61Q 19/08* (2013.01); *C12N 2501/999* (2013.01)

(58) Field of Classification Search
None
See application file for complete search history.

(56) References Cited

U.S. PATENT DOCUMENTS

2021/0052657 A1\* 2/2021 Glassberg Csete .. C12N 5/0663

FOREIGN PATENT DOCUMENTS

| CN | 111228569 A | 6/2020 |
|---|---|---|
| CN | 112190536 A | 1/2021 |
| CN | 113699103 A | 11/2021 |
| JP | 2022-20814 A | 2/2022 |
| WO | 2011/034106 A1 | 3/2011 |
| WO | 2022/025559 A1 | 2/2022 |

OTHER PUBLICATIONS

Gugliandolo, Agnese et al. Dental Mesenchymal Stem Cell Secretome: An Intriguing Approach for Neuroprotection and Neuroregeneration. International Journal of Molecular Science 2022, 23, 456. (Year: 2022).*

Yuhua Gao et al., "Isolation and Characterization of Chicken Dermis-Derived Mesenchymal Stem/Progenitor Cells", BioMed Research International, Hindawi Publishing Corporation, vol. 2013, Article ID 626258, pp. 1-8, 2013.

Ryosuke Mizuta et al., "Extracellular vesicle hybrid engineering for DDS and medical application", Drug Delivery System, 2021, vol. 36-2, pp. 90-99, https://www.jstage.jst.go.jp/article/dds/36/2/36_90/_pdf/-char/ja, 2021.

Yafei Wang, et al., Exosomes from embryonic mesenchymal stem cells alleviate osteoarthritis through balancing synthesis and degradation of cartilage extracellular matrix., Stem Cell Research & Therapy (2017) 8:189.

Yoon-Jin Kim, et al., Exosomes derived from human umbilical cord blood mesenchymal stem cells stimulates rejuvenation of human skin., Biochemical and Biophysical Research Communications 493 (2017) pp. 1102-1108.

Chin, Y.-T. et al., "2, 3, 5, 4'- tetrahydroxystilbene-2-O-β-D-glucoside-stimulated dental pulp stem cells-derived conditioned medium enhances cell activity and anti-inflammation", Journal of Dental Sciences, vol. 16, 2021, pp. 586~598, 2021.

C.-Y. Lin et al., "2,3,5,4'-Tetrahydroxystilbene-2-O-β-glucoside potentiates self-renewal of human dental pulp stem cells via the AMPK/ERK/SIRT1 axis", International Endodontic Journal, vol. 51, 2018, XP071473062, pp. 1159-1170, John Wiley & Sons Ltd., 2018.

Yu-Tang Chin et al., "2,3,5,4'-Tetrahydroxystilbene-2-O-β-glucoside Isolated from Polygoni Multiflori Ameliorates the Development of Periodontitis", Mediators of Inflammation vol. 2016, XP093048920, pp. 1~12 and back cover page, Hindawi Publishing Corporation. (http://dx.doi.org/10.1155/2016/6953459), 2016.

Lingling Zhang et al., "Promotive effects of tetrahydroxystilbene glucoside on the differentiation of neural stem cells from the mesencephalon into dopaminergic neurons", Neuroscience Letters vol. 742, 2021, XP086430451, pp. 1-7, ELSEVIER. (https://doi.org/10.1016/j.neulet.2020.135520), 2021.

\* cited by examiner

*Primary Examiner* — Nghi V Nguyen
(74) *Attorney, Agent, or Firm* — Winston Hsu

(57) ABSTRACT

Disclosed herein is a method for producing exosomes, which includes cultivating avian embryo-derived mesenchymal stem cells in a culture medium containing 2,3,4',5-tetrahydroxystilbene-2-O-β-D-glucoside, so as to obtain a cell culture of AMSCs, and subjecting the cell culture of AMSCs to a separation treatment, so as to obtain the exosomes. An exosome produced by the method, and a method for improving a skin condition using the exosome are also disclosed.

11 Claims, 11 Drawing Sheets
Specification includes a Sequence Listing.

EXOSOME AND PREPARATION PROCESS AND USE THEREOF

CROSS-REFERENCE TO RELATED APPLICATION

This application claims priority of Taiwanese Patent Application No. 111105325, filed on Feb. 14, 2022.

FIELD

The present disclosure relates to a method for producing exosomes, and an exosome prepared by the method. The present disclosure also relates to use of the exosome to improve a skin condition.

BACKGROUND

Exosomes are nanosized vesicles secreted by cells, and belong to extracellular vesicles (EVs). Exosomes are present in various biological fluids (such as amniotic fluid, urine, and blood), and are rich in proteins, lipids, mRNAs, and miRNAs.

To investigate biological activity of exosomes, size-selective separation (e.g., filtration, dialysis, and chromatography) and density-selective separation (e.g., centrifugation) are often used to separate exosomes from stem cell cultures.

Previous studies demonstrated that exosomes produced by different types of stem cells have different biological activities. For example, it has been reported in Wang Y. et al. (2017), *Stem Cell Res. Ther.,* 8:189 that the exosomes from human embryonic stem cell-induced mesenchymal stem cells (ESC-MSCs) exert a beneficial therapeutic effect on osteoarthritis (CA) by balancing the synthesis and degradation of chondrocyte extracellular matrix (ECM). In addition, Kim Y. J. et al. (2017), *Biochem. Biophys. Res. Commun.,* 493:1102-1108 discloses that the exosomes from human umbilical cord blood-derived mesenchymal stem cells (UCB-MSCs) can be absorbed into human skin and promote collagen I and elastin synthesis in the skin, and hence are essential to skin rejuvenation.

In spite of the aforesaid reports, due to the high demand for exosomes in the market, there is still a need to develop a new strategy that can be utilized for mass production of exosomes.

SUMMARY

Therefore, in a first aspect, the present disclosure provides a method for producing exosomes which can alleviate at least one of the drawbacks of the prior art.

The method includes cultivating avian embryo-derived mesenchymal stem cells (AMSCs) in a culture medium containing 2,3,4',5-tetrahydroxystilbene-2-O-β-D-glucoside (THSG), so as to obtain a cell culture of AMSCs; and subjecting the cell culture of AMSCs to a separation treatment, so as to obtain the exosomes.

In a second aspect, the present disclosure provides an exosome, which can alleviate at least one of the drawbacks of the prior art, and which is produced by the aforesaid method.

In a third aspect, the present disclosure provides a method for improving a skin condition, which can alleviate at least one of the drawbacks of the prior art, and which includes administering to a subject in need thereof a composition containing the aforesaid exosome.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
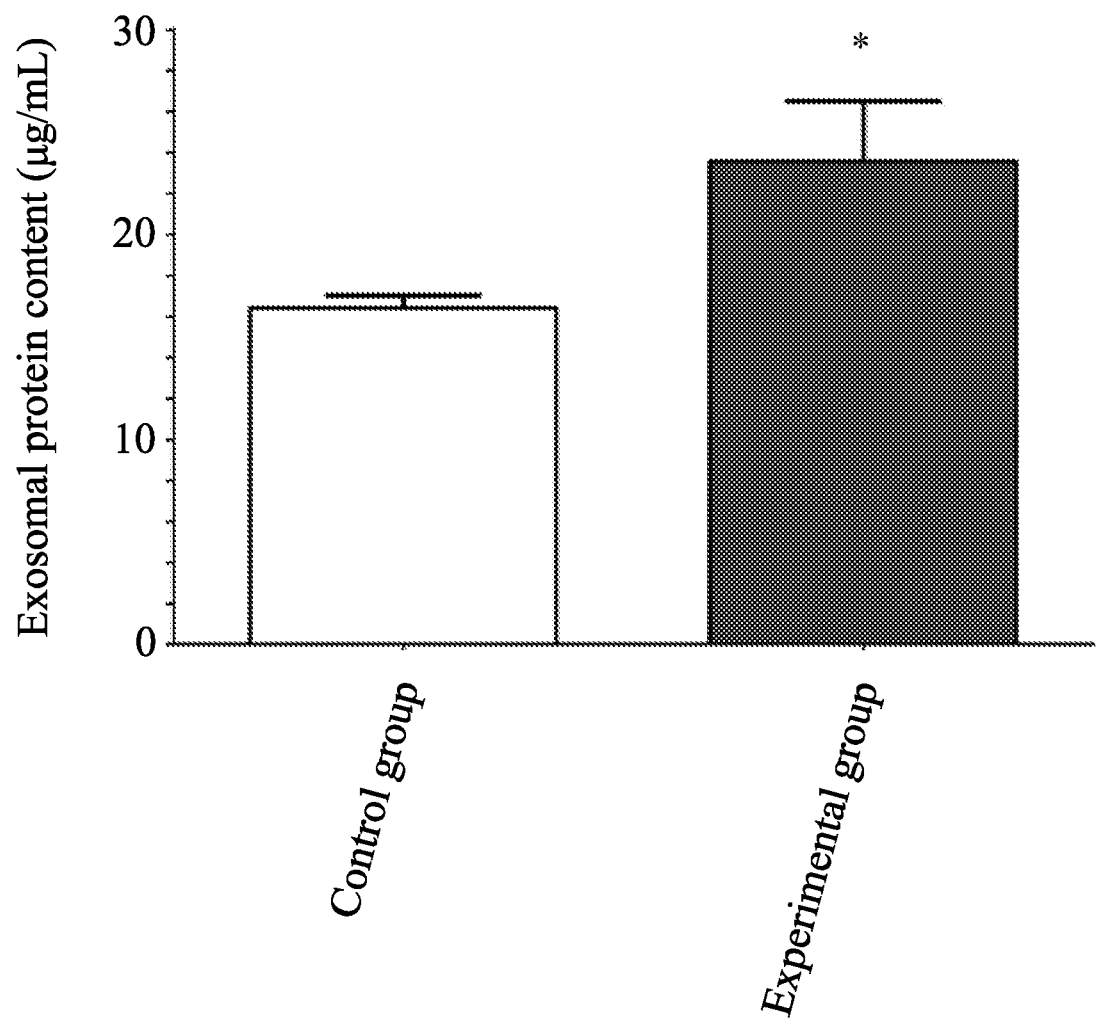
FIG. 1 shows the exosomal protein content in each group of Example 2, infra, in which the symbol "*" represents $p<0.05$ (compared with the control group)

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

The present disclosure provides a method for producing exosomes, which includes:

cultivating avian embryo-derived mesenchymal stem cells (AMSCs) in a culture medium containing 2,3,4',5-tetrahydroxystilbene-2-O-β-D-glucoside (THSG), so as to obtain a cell culture of AMSCs; and subjecting the cell culture of AMSCs to a separation treatment, so as to obtain the exosomes.

According to the present disclosure, the exosomes may be obtained in an amount not lower than $1\times10^8$ particles/mg. In certain embodiments, the exosomes may be obtained in an amount ranging from $1\times10^9$ particles/mg to $1\times10^{10}$ particles/mg. In an exemplary embodiment, the amount of the exosomes is $5.08\times10^9$ particles/mg.

According to the present disclosure, the AMSCs may be present in an amount ranging from $8.3\times10^7$ cells to $8.3\times10^9$ cells. In certain embodiments, the amount of the AMSCs is $1\times10^8$ cells.

According to the present disclosure, the culture medium may contain THSG at a concentration ranging from 0.1 μM to 50 μM. In certain embodiments, the culture medium contains 25 μM of THSG.

According to the present disclosure, THSG may be isolated from a plant material, e.g., *Polygonum multiflorum* using technology well known to those skilled in the art. In this regard, those skilled in the art may refer to journal articles, e.g., Tsai P. W. et al. (2018), *Molecules*, 23(3):571.

In certain embodiments, THSG suitable for use in this disclosure may be obtained as commercial products, e.g., stilbene glycoside (Cat. No. BP0039) purchased from Chengdu Biopurify Phytochemicals Ltd.

As used herein, the term "cultivating" can be used interchangeably with other terms such as "cultivation" and "culturing".

It should be noted that the procedures and operating conditions for cultivating the AMSCs may be adjusted according to practical requirements. In this regard, those skilled in the art may refer to journal articles, e.g., Gao Y. et al. (2013), *Biomed. Res. Int.*, doi: 10.1155/2013/626253.

According to the present disclosure, the culture medium suitable for culturing the AMSCs may include, but is not limited to, Dulbecco's Modified Eagle's Medium (DMEM) supplemented with various nutrients to enhance AMSCs growth. Additionally, the culture medium may be supplemented with additives such as horse, calf or fetal bovine serum.

According to the present disclosure, the cultivation of the AMSCs may be performed at a temperature ranging from 36° C. to 37° C. In certain embodiments, the cultivation of the AMSCs is performed at a temperature of 37° C.

According to the present disclosure, the cultivation of the AMSCs may be performed for a time period ranging from, 24 hours to 96 hours. In certain embodiments, the cultivation of the AMSCs is performed for a time period of 36 hours.

According to the present disclosure, the procedures and operating conditions for the separation treatment may be adjusted according to practical requirements. In this regard, those skilled in the art may refer to journal articles, e.g., Wang Y. et al. (2017), supra.

According to the present disclosure, the separation treatment may be selected from the group consisting of size-selective separation and density-selective separation.

According to the present disclosure, the size-selective separation may be selected from the group consisting of filtration (such as ultrafiltration and tangential flow filtration (TFF)), dialysis (such as diafiltration), chromatography (such as size-exclusion chromatography (SEC)), and combinations thereof. In certain embodiments, the size-selective separation is a combination of tangential flow filtration (TFF) and size-exclusion chromatography (SEC).

According to the present disclosure, TFF may be performed using a filtration membrane having a molecular weight cut-off (MWCO) value ranging from 100 kDa to 500 kDa. In certain embodiments, TFF is performed using a filtration membrane having a molecular weight cut-off (MWCO) value of 500 kDa.

According to the present disclosure, TFF may be performed at a flow rate ranging from 50 mL/min to 200 mL/min. In certain embodiments, IFF is performed at a flow rate ranging from 80 mL/min to 120 mL/min.

According to the present disclosure, SEC may be performed at a column temperature ranging from 15° C. to 25° C. In certain embodiments, SEC is performed at a column temperature of 25° C.

According to the present disclosure, the density-selective separation may be a centrifugation treatment selected from the group consisting of ultracentrifugation and density gradient centrifugation.

The present disclosure also provides an exosome, which is prepared by the abovementioned method.

According to the present disclosure, the exosome may have a particle size ranging from 50 nm to 200 nm. In certain embodiments, the exosome has a particle size ranging from 50 nm to 150 nm.

According to the present disclosure, the exosome may have an average particle size ranging from 50 nm to 100 nm. In certain embodiments, the exosome has an average particle size of 72 nm.

According to the present disclosure, the exosome may be subjected to a drying treatment using techniques well-known to those skilled in the art, so as to obtain a product in a powder form. Examples of the drying treatment may include, but are not limited to, a freeze-drying treatment, a spray-drying treatment, a vacuum drying treatment, and a fluid bed drying. In certain embodiments, the exosome is subjected to a freeze-drying treatment.

Moreover, the present disclosure provides a method for improving a skin condition, which includes administering to a subject in need thereof a composition containing the aforesaid exosome.

As used herein, the term "administration" or "administering" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the skin condition is selected from the group consisting of wound, skin aging, hair loss, skin inflammation, and combinations thereof.

As used herein, the term "skin aging" is intended to encompass naturally occurring intrinsic skin aging, and extrinsic skin aging caused by environmental factors (such as ultraviolet radiation). Examples of the skin aging may include, but are not limited to, telangiectasia, thinner epidermis, skin atrophy, reduction of collagen fibers and elastic fibers, elastosis, deterioration of skin elasticity, poor skin texture, dryness, wrinkle formation, and pigmentary change (such as lentigines, freckles, hypopigmentation or hyperpigmentation).

According to the present disclosure, the composition may be formulated as a cosmeceutical composition. The cosmeceutical composition may further include the aforesaid pharmaceutically acceptable carrier and/or a cosmetically acceptable adjuvant, and may be made into an external preparation suitable for skincare or makeup using technology well-known to those skilled in the art.

Examples of the cosmetically acceptable adjuvant may include, but are not limited to, solvents, gelling agents, active agents, antioxidants, screening agents, surfactants, coloring agents, thickening agents, fillers, fragrances, and odor absorbers. The choice and amount of the cosmetically acceptable adjuvant are within the expertise of those skilled in the art.

Examples of the external preparation suitable for skincare or makeup include, but are not limited to, aqueous solutions, aqueous-alcohol solutions or oily solutions, oil-in-water types, water-in-oil types or complex emulsions, gels, ointments, creams, masks, patches, packs, bandages, liniments, powders, aerosols, sprays, lotions, serums, pastes, foams, dispersions, suspensions, drops, mousses, salves, sunblocks, tonic water, foundations, eyeshadows, and the like.

According to the present disclosure, the composition may be prepared into a pharmaceutical composition in a dosage form suitable for, e.g., parenteral or oral administration, using technology well known to those skilled in the art.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intramuscular injection, intraepidermal injection, subcutaneous injection, intradermal injection, and intralesional injection.

According to the present disclosure, the dosage form suitable for oral administration includes, but is not limited to, sterile powders, tablets, troches, lozenges, pellets, capsules, dispersible powders or granules, solutions, suspensions, emulsions, syrup, elixir, slurry, and the like.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the aforesaid agents are within the expertise and routine skills of those skilled in the art.

The dose and frequency of administration of the pharmaceutical composition may vary depending on the following factors: the severity of the illness or disorder to be treated, routes of administration, and age, physical condition and response of the subject to be treated. In general, the pharmaceutical composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials 1. 2,3,4',5-tetrahvdroxystilbene-2-O-β-D-glucoside (THSG) used in the following experiments was prepared according to the procedures described in Tsai P. W. et al. (2018), supra.

2. Avian Embryo-Derived Mesenchymal Stem Cells (AMSCs) and human dental pulp stem cells (DPSCs) were prepared according to the procedures described in Gao Y. et al. (2013), supra and Lin C. Y. et al. (2019), *J. Endod.*, 45:435-441, respectively.

3. Human Skin Fibroblasts (HSFs)

The HSFs used in the following examples were purchased from the Bioresource Collection and Research Center (BCRC) of the Food Industry Research and Development institute (FIRDI) (No. 331, Shih-Pin Rd., Hsinchu City 300, Taiwan). The HSFs were grown in a 75T flask containing Dulbecco's Modified Eagle's Medium (DMEM) (Corning®, Cat. No. 10-017-CM) supplemented with 10% fetal bovine serum (FBS), 100 U/mL penicillin, and 100 µg/mL streptomycin. The HSFs were cultivated in an incubator with culture conditions set at 37° C. and 5% $CO_2$. Medium change was performed every two to three days. Cell passage was performed when the cultured cells reached 80% to 90% of confluence.

4. Human Follicle Dermal Papilla Cells (HFDPCs)

The HFDPCs used in the following examples were purchased from PromoCell GmbH (Heidelberg, Germany) (Cat. No. C-12071). The HFDPCs were grown in a 75T flask containing follicle dermal papilla cell growth medium (FDPCGM) (PromoCell GmbH, Cat. No. C-26501) supplemented with 1% growth medium supplement mix (PromoCell GmbH, Cat. No. C-39625), 100 U/mL penicillin, and 100 µg/mL streptomycin. The HFDPCs were cultivated in an incubator with culture conditions set at 37° C. and 5% $CO_2$. Medium change was performed every two to three days. Cell passage was performed when the cultured cells reached 80% to 90% of confluence.

General Procedures

1. Statistical Analysis

All the experiments described below were performed in triplicates. The experimental data of all the test groups are expressed as mean±standard error of the mean (SEM). Statistical analysis was conducted using IBM® SPSS® Statistics version 19.0 (SPSS Inc., IL, USA). All the data were analyzed using two-tailed Student's t-test, so as to assess the differences between the groups. Statistical significance is indicated by $p<0.05$.

Example 1. Evaluation for the Effect of THSG on Production of Exosomes from AMSCs The AMSCs prepared in section 2 of "General Experimental Materials" were divided into 2 groups, including one control group and one experimental group. The AMSCs of each group was incubated in a 10-cm Petri dish containing 5 mL of DMEM supplemented with 2.5 FBS at $5\times10^6$ cells/well, followed by cultivation in an incubator (37° C., 5% $CO_2$) for 48 hours. The resultant cell culture of each group has a cell number of $1\times10^8$. Next, the cell culture of the experimental group was replaced with a fresh DMEM medium containing 25 μM THSG, while the cell culture of the control group was replaced with a fresh DMEM medium without THSG. Each group was cultivated in an incubator (37° C., 5% $CO_2$) for 36 hours.

Thereafter, the liquid cell culture of each group was subjected to a centrifugation treatment performed at 1,000 g for 10 minutes to remove precipitates. The centrifugation treatment was repeated twice. The resultant supernatant was collected, and then subjected to filtration using a filter (mesh: 0.22 μm), so as to obtain a first filtrate.

The first filtrate of each group was subjected to tangential flow filtration (TFF) to obtain a second filtrate. TFF was performed using a mini tangential flow filtration system equipped with a pump (rotation speed: 80-120 mL/min) and hollow fiber filter modules with 500 kDa modified polyethersulfone (mPES).

The second filtrate of each group was subjected to filtration using a filter (mesh: 0.22 μm), so as to obtain a third filtrate. The third filtrate of each group was subjected to size-exclusion chromatography (SEC) analysis to obtain an eluate containing exosomes. SEC analysis was performed using a SEC qEV column (column temperature: 25° C.), and phosphate-buffered saline (PBS) was used as an eluent.

The eluate of each group was subjected to a freeze-drying treatment, so as to obtain a dried exosome powder of the experimental group and a dried exosome powder of the control group.

Example 2. Analysis of Exosome Components

A. Determination of Exosomal Protein Content 100 mg of a respective one of the two dried exosome powders prepared in Example 1 was mixed with a RIPA lysis buffer, followed by determining the exosomal protein content using Piercer™ BCA Protein Assay Kit (Thermo Fisher Scientific Inc., Cat. No. 23225) according to the manufacturer's instructions.

In addition, bovine serum albumin (BSA) was used as a control standard (which was provided at concentrations of 0, 1.953, 3.90625, 7.8125, 15.625, 31.25, 62.5, 125, and 250 μg/mL), and was subjected to the same analysis.

Referring to FIG. 1, the exosomal protein content determined in the experimental group was significantly higher than that determined in the control group.

B. Determination of Exosomal RNA Content 100 mg of a respective one of the two dried exosome powders prepared in Example 1 was subjected to determination of exosomal RNA content using qEV RNA Extraction Kit (IZON, Cat. No. RXT01) according to the manufacturer's instructions.

Figure 2:
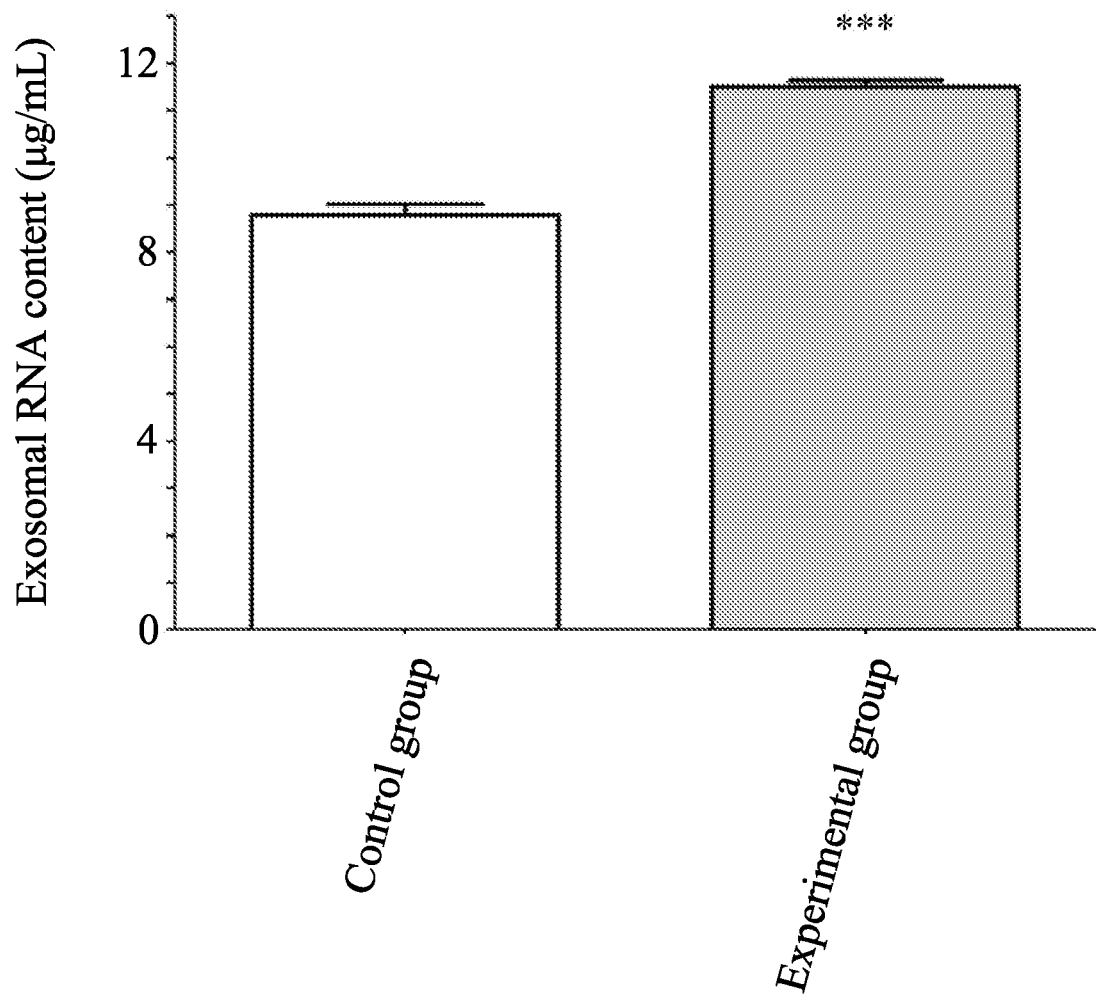
FIG. 2 shows the exosomal RNA content in each group of Example 2, infra, in which the symbol "***" represents $p<0.001$ (compared with the control group)

Referring to FIG. 2, the exosomal RNA content determined in the experimental group was significantly higher than that determined in the control group.

Example 3. Evaluation for the Effect of THSG on Production of Exosomes from Different Stem Cells The DPSCs prepared in section 2 of "General Experimental Materials" were subjected to the same THSG treatment, exosome isolation, and freeze-drying treatment as described in Example 1, so as to obtain a dried exosome powder from the DPSCs (serving as a comparative group).

18 mg of the respective one of the dried exosome powder of the experimental group prepared in Example 1 and the dried exosome powder of the comparative group was mixed with distilled water, followed by determination of content and particle size using a qNano system (Izon Science Ltd.) based on tunable resistive pulse sensing (tRPS) technology.

As shown in Table 1 below, the exosome content determined in the experimental group was significantly higher than that determined in the comparative group. In addition, the exosome of the experimental group had a particle size ranging from 53 nm to 245 nm, and had an average particle size of 72 nm.

TABLE 1

| Exosome | Experimental group | Comparative group |
| --- | --- | --- |
| Content (particles/mg) | $5.08 \times 10^9$ | $4.16 \times 10^7$ |
| Particle size (nm) | 53-245 | 76-436 |
| Average particle size (nm) | 72 | 102 |

These results indicate that the method of the present disclosure can produce a high content of exosomes, and the exosomes thus obtained have a relatively small particle size.

Example 4. Evaluation of Anti-Wrinkle Effect of Excosome According to this Disclosure Materials:
1. Preparation of Exosome Suspension A suitable amount of the dried exosome powder of the experimental group prepared in Example 1 was suspended in sterile ultrapure water, so as to obtain an exosome suspension.

Methods:

The HSFs prepared in section 3 of "General Experimental Materials" were divided into 4 groups, including one control group and three experimental groups (i.e., experimental groups 1 to 3). Each group of the HSFs was incubated in a respective well of 6-well culture plates containing 2 mL of DMEM supplemented with 10% FBS at $1\times10^5$ cells/well, followed by cultivation in an incubator (37° C., 5% $CO_2$) for 24 hours.

Thereafter, each of the cell cultures of the three experimental groups and the control group was replaced with 2 mL of a fresh DMEM medium containing 0.25% charcoal stripped fetal bovine serum (CS-FBS) (Cat. No. 12676029, Thermo Fisher Scientific Inc.). Next, each of the cell cultures of the three experimental groups was treated with a suitable amount of the exosome suspension prepared in section 1 of "Materials" of this example so that the respective cell culture had a final exosome concentration as shown in Table 2. In addition, the cell culture of the control group received no treatment.

TABLE 2

| Group | Final exosome concentration (μg/mL) |
| --- | --- |
| Control group | — |
| Experimental group 1 | 0.07 |
| Experimental group 2 | 0.7 |
| Experimental group 3 | 70 |

Each group was cultivated in an incubator (37° C., 5% $CO_2$) for 48 hours. After centrifugation at 5,000 rpm for 5 minutes, the resultant cell pellet was collected, and was then subjected to total RNA extraction using GENEzolTr™ TriRNA Pure Kit (Geneaid, Cat. No. GZXD200) in accordance with the manufacturer's instructions. The resultant RNA of the respective group was used as a template for synthesizing cDNA by reverse transcription polymerase chain reaction (RT-PCR) using RevertAid H Minus First Strand cDNA Synthesis Kit (Thermo Fisher Scientific Inc., Cat. No. K1631) in accordance with the manufacturer's instructions.

The thus obtained cDNA, serving as a DNA template, was subjected to quantitative real-time PCR based on SYBR-Green I fluorescence, which was performed on a CFX Connect™ Real-Time PCR Detection System (Bio-Rad Laboratories, Inc.) using designed primer pairs specific for COL1A1 gene, COL3A1 gene, and ELN gene shown in Table 3 and the reaction conditions shown in Table 4. 18S rRNA gene was used as an endogenous control in the quantitative analysis of real-time PCR to normalize the gene expression data.

The resultant PCR product was subjected to determination of fluorescence intensity, followed by calculating the cycle threshold (Ct) value of each of COL1A1 gene, COL3A1 gene, and ELN gene. Quantitative real-time PCR data were analyzed using the comparative Ct method. Briefly, the Ct value of each of COL1A1 gene, COL3A1 gene, and ELN gene in each group was normalized with that of 18S rRNA gene, and the relative mRNA expression level of each of COL1A1 gene, COL3A1 gene, and ELN gene was further calculated using the following Equation (I):

$$A = B/C \quad (I)$$

where
A=relative mRNA expression level of COL1A1 gene, COL3A1 gene, or ELN gene
B=normalized ct value of COL1A1 gene, COL3A1 gene, or ELM gene in respective group
C=normalized ct value of COL1A1 gene, COL3A1 gene, or ELN gene in control group The data thus obtained were analyzed according to the method described in section 1 of "General Procedures".

TABLE 3

| Target gene | Primer | Nucleotide sequence (5'→3') | Size of PCR product (bp) |
|---|---|---|---|
| COL1A1 gene (NCBI accession no. NM 000088.4) | Forward primer COL1A1-F | gtcagatgggcccccg (SEQ ID NO: 1) | 84 |
| | Reverse primer COL1A1-R | caccatcatttccacgagca (SEQ ID NO: 2) | |
| COL3A1 gene (NCBI accession no. NM 000090) | Forward primer COL3A1-F | gaggatggttgcacgaaacac (SEQ ID NO: 3) | 70 |
| | Reverse primer COL3A1-R | cagccttgcgtgttcgatatt (SEQ ID NO: 4) | |
| ELN gene (NCBI accession no. M36860) | Forward primer ELN-F | caggtgcggtggttcctc (SEQ ID NO: 5) | 81 |
| | Reverse primer ELN-R | ctgggtatacacctggcagc (SEQ ID NO: 6) | |
| 18S rRNA gene (NCBI accession no. NR 003286) | Forward primer 18s-F | gtaacccgttgaaccccatt (SEQ ID NO: 7) | 130 |
| | Reverse primer 18s-R | ccatccaatcggtagtagcg (SEQ ID NO: 8) | |

TABLE 4

| Reaction mix | Volume (μL) |
|---|---|
| cDNA (0.1 μg/μL) | 2 |
| Forward primer (100 nM) | 1 |
| Reverse primer (100 nM) | 1 |
| 2X QuantiNova ™ SYBR ® Green PCR Master Mix (QIAGEN) | 10 |
| Sterile water | 6 |

Operation conditions: denaturation at 95° C. for 5 minutes, followed by forty cycles of the following reactions: denaturation at 95° C. for 5 seconds, annealing and extension at 60° C. for 10 seconds.

Figure 3:
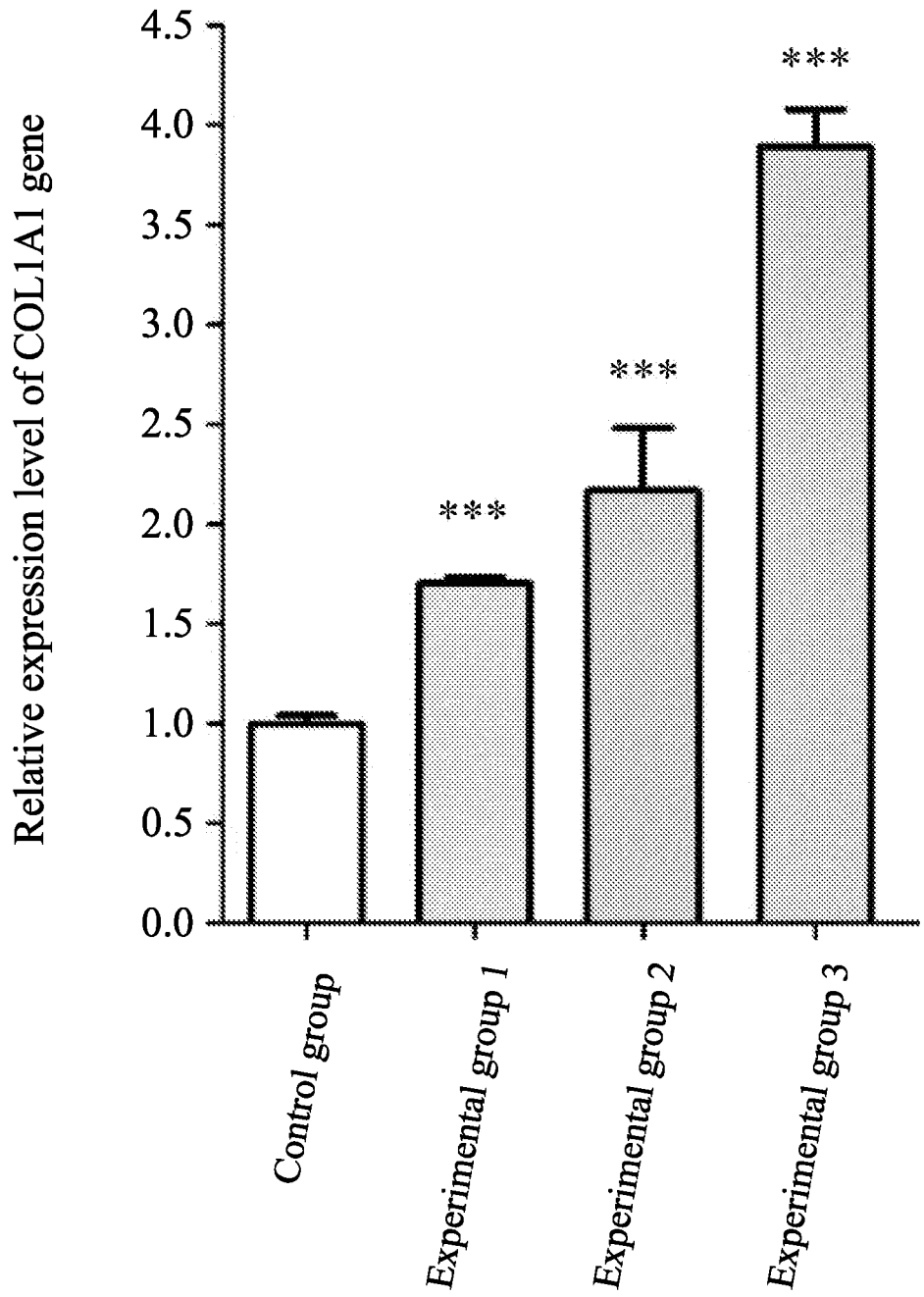
FIG. 3 shows the relative expression level of COL1A1 gene in each group of Example 4, infra, in which the symbol "***" represents $p<0.001$ (compared with the control group)
Figure 4:
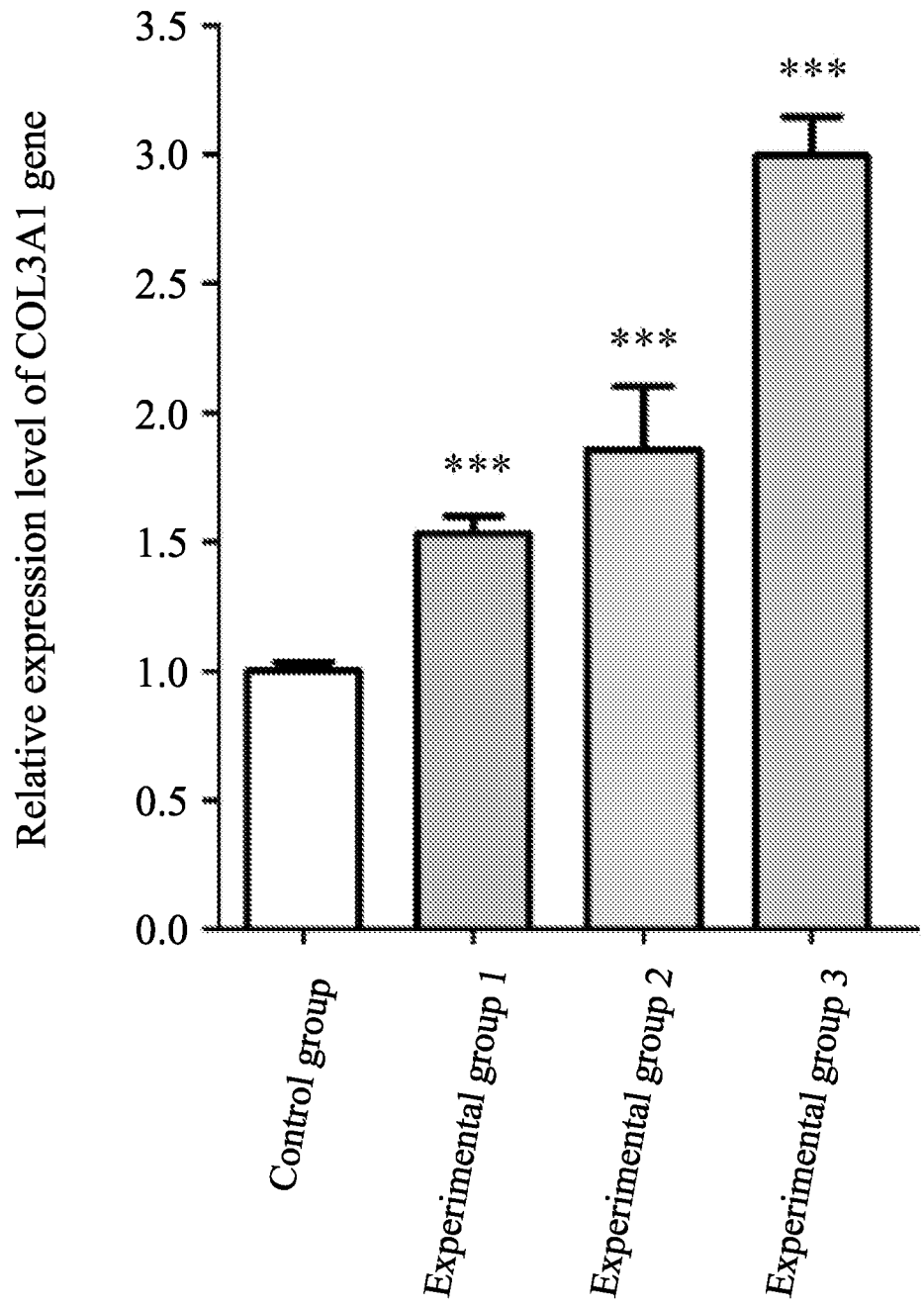
FIG. 4 shows the relative expression level of COL3A1 gene in each group of Example 4, infra, in which the symbol "***" represents $p<0.001$ (compared with the control group)
Figure 5:
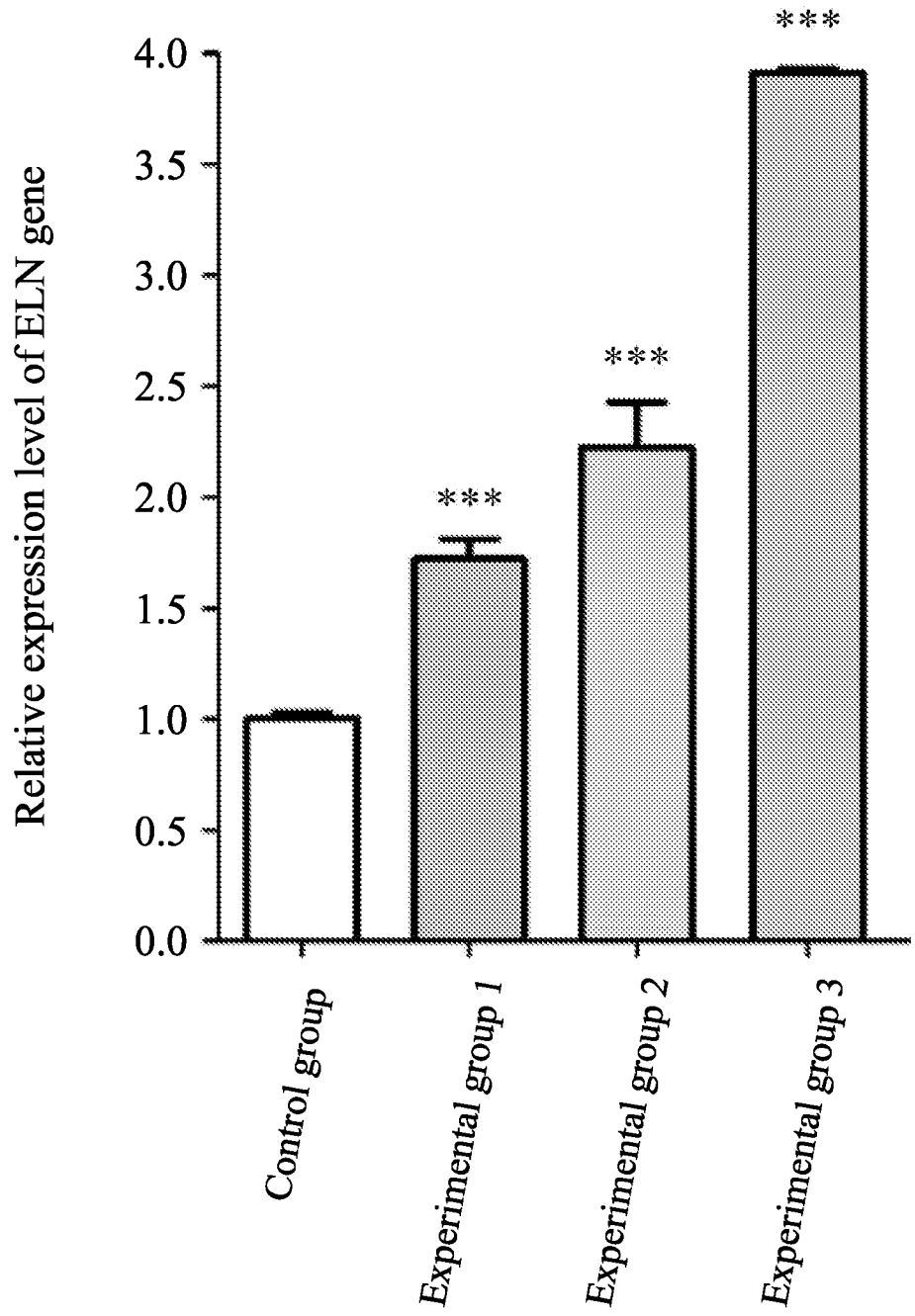
FIG. 5 shows the relative expression level of ELN gene in each group of Example 4, infra, in which the symbol "***" represents $p<0.001$ (compared with the control group)

Results:

Referring to FIGS. 3 to 5, the relative mRNA expression levels of COL1A1 gene, COL3A1 gene, and ELN gene determined in the experimental groups 1 to 3 were higher than those determined in the control group. Moreover, the relative mRNA expression levels of COL1A1 gene, COL3A1 gene, and ELN gene determined in the experimental group 3 were significantly higher than those determined in the experimental group 1.

These results indicate that the exosomes produced by the method of the present disclosure can promote the secretion of collagen and elastin from dermal fibroblasts in a dose-dependent manner, thereby achieving anti-wrinkle effect.

Example 5. Evaluation for the Effect of Exosome According to this Disclosure on Promotion of Skin Regeneration Methods:

The HSFs prepared in section 3 of "General Experimental Materials" were divided into 2 groups, including one control group and one experimental group. Each group of the HSFs was incubated in a respective well of 96-well culture plates containing 100 μL of DMEM supplemented with 10% FBS at $5\times10^3$ cells/well, followed by cultivation in an incubator (37° C., 5% $CO_2$) for 24 hours.

Thereafter, each of the cell cultures of the experimental group and the control group was replaced with 100 μL of a fresh DMEM medium containing 0.25% CS-FBS. Next, the cell culture of the experimental group was treated with a suitable amount of the exosome suspension prepared in section 1 of "Materials" of Example 4, so that the cell culture had a final exosome concentration of 70 μg/mL. In addition, the cell culture of the control group received no treatment.

Each group was cultivated in an incubator (37° C., 5% $CO_2$) for 72 hours. Next, each of the cell cultures of the experimental group and the control group was replaced with a growth medium containing 20% MTS solution (CellTiter 96® AQueous One Solution Cell Proliferation Assay Kit) (Promega Corporation, Cat. No. G3581), followed by cultivation in an incubator (37° C., 5% $CO_2$) for 2 hours.

The respective resultant cell culture was subjected to determination of absorbance at a wavelength of 490 nm ($OD_{490}$) by a VersaMax ELISA reader (Molecular Devices). The cell viability rate (%) was calculated using the following Equation (II):

$$D=(E/F)\times100 \tag{II}$$

where

D=cell viability rate (I)
E=$OD_{490}$ value of respective group
F=$OD_{490}$ value of control group The data thus obtained were analyzed according to the method described in section 1 of "General Procedures".

Figure 6:
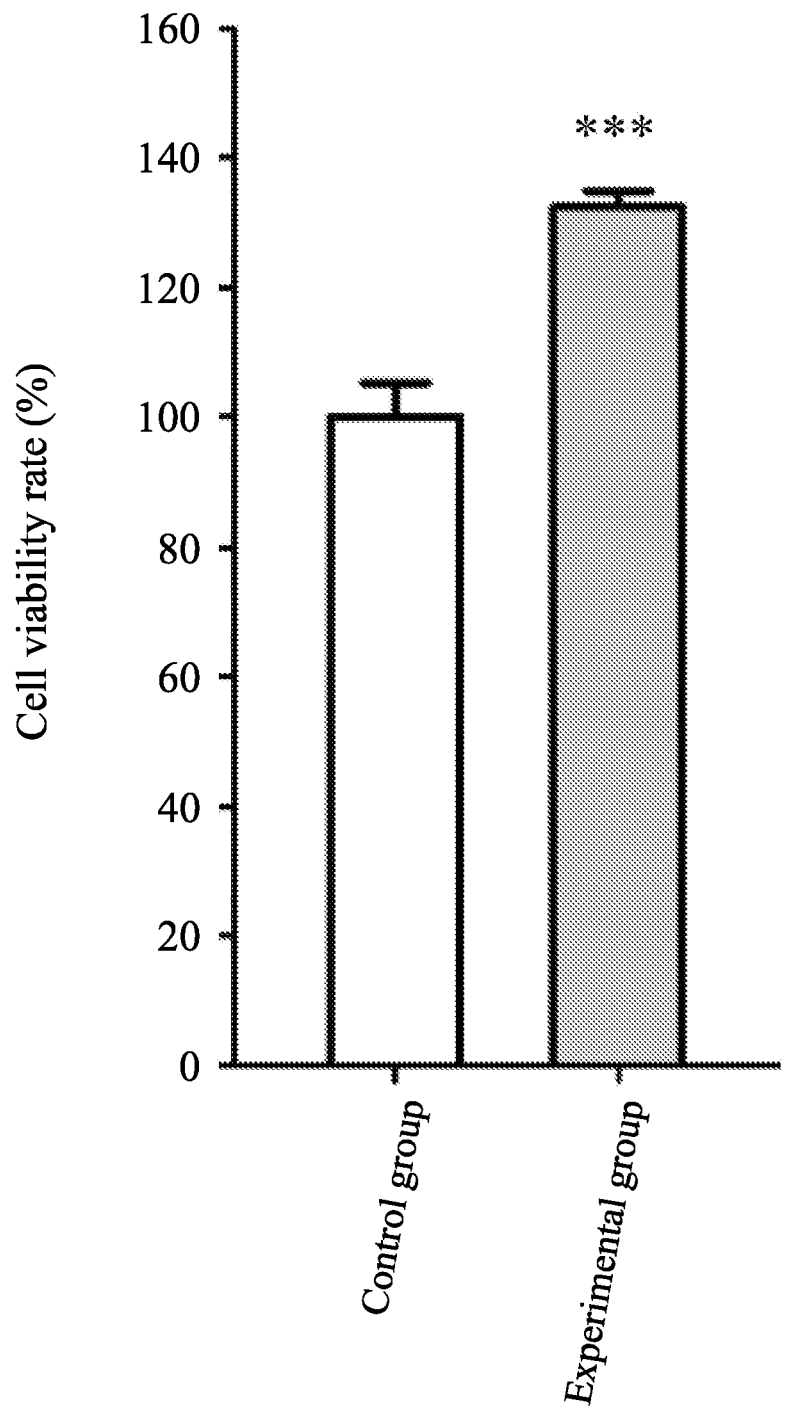
FIG. 6 shows the cell viability rate in each group of Example 5, infra, in which the symbol "***" represents $p<0.001$ (compared with the control group)

Results:

Referring to FIG. 6, the cell viability rate determined in the experimental group was significantly higher than that determined in the control group. This result indicates that the exosomes produced by the method of the present disclosure can improve skin regeneration by promoting the proliferation of skin fibroblasts.

Example 6. Evaluation for the Effect of Exosome According to this Disclosure on Promotion of Wound Healing Methods:

The HSFs prepared in section 3 of "General Experimental Materials" were divided into 2 groups, including one control group and one experimental group. Each group of the HSFs was incubated in a respective well of 24-well culture plates containing 500 μL of DMEM supplemented with 10% FBS at $2.5\times10^5$ cells/well, followed by cultivation in an incubator (37° C., 5% $CO_2$) for 24 hours.

Thereafter, each of the cell cultures of the experimental group and the control group was replaced with a fresh DMEM medium, followed by cultivation in an incubator (37° C., 5% $CO_2$) for 24 hours. Next, the cell culture of each group was scraped along the diameter of the corresponding well by using sterile forceps to create a cell-free wound area of approximately 500 μm. Subsequently, each of the cell cultures of the experimental group and the control group was replaced with 500 μL of a fresh DMEM medium containing 0.25% CS-FBS. Then, the cell culture of the experimental group was treated with a suitable amount of the exosome suspension prepared in section 1 of "Materials" of Example 4, so that the cell culture had a final exosome concentration of 70 μg/mL. In addition, the cell culture of the control group received no treatment.

Thereafter, the cell culture of each group was subjected to cultivation in an incubator (37° C., 5% $CO_2$) for 24 hours. Before performing the cultivation and at the $24^{th}$ hour after start of the cultivation, the wound area in each group was observed under an inverted microscope (Manufacturer: Olympus Corporation; Model no.: CKX53) at a magnification of 40× and then photographed using a digital camera (Manufacturer: Olympus Corporation; Model no.: EP50).

Figure 7:
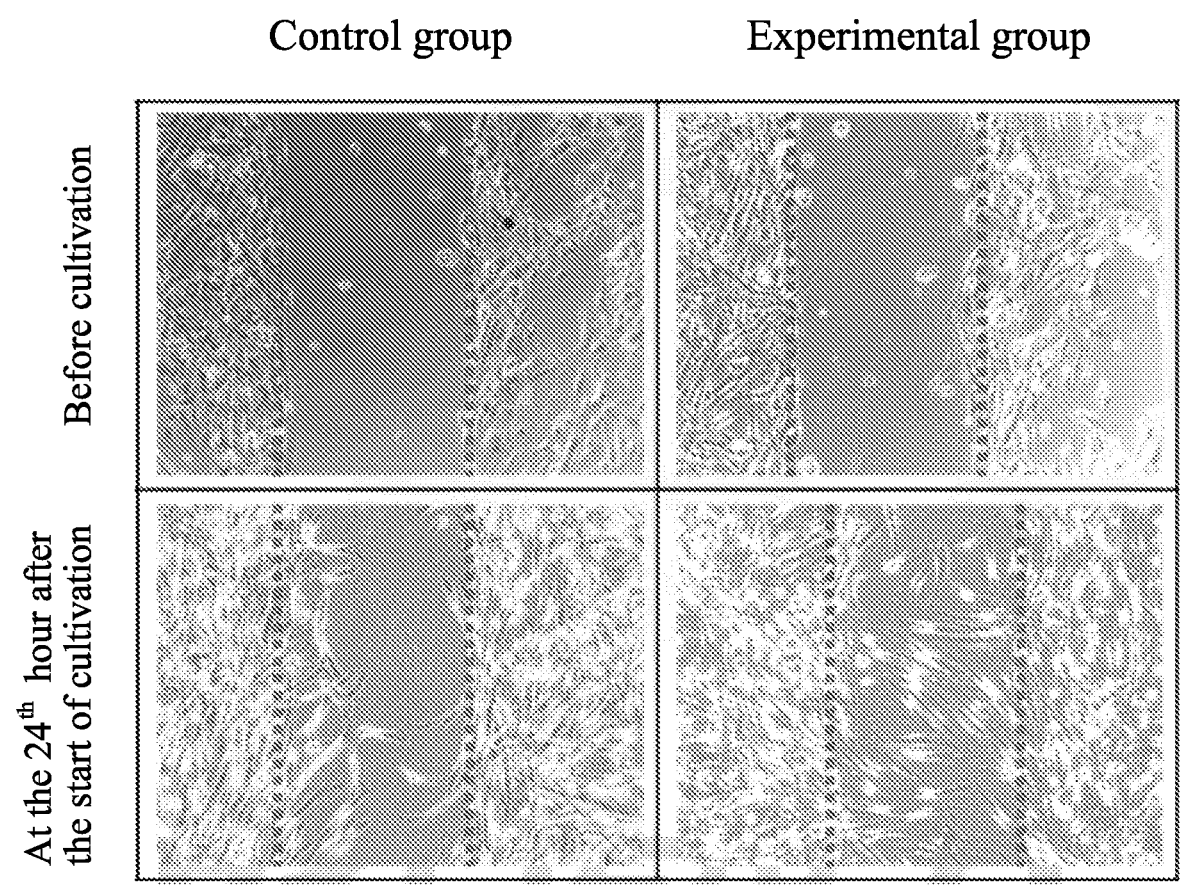
FIG. 7 shows the result obtained from observation of wound healing in each group of Example 6, infra.

Results:

Referring to FIG. 7, in comparison with the control group, wound healing was clearly observed in the experimental group at the $24^{th}$ hour after start of the cultivation. This result indicates that the exosomes produced by the method of the present disclosure can effectively improve fibroblast-mediated wound closure, and hence can exhibit an excellent effect in promotion of wound healing.

Example 7. Evaluation for the Effect of Exosome According to this Disclosure on Improving Hair Loss Methods:

The HFDPCs prepared in section 4 of "General Experimental Materials" were divided into 2 groups, including one control group and one experimental group. Each group of the HFDPCs was incubated in a respective well of 96-well culture plates containing 100 μL of FDPCGM supplemented with 1% growth medium supplement mix at $5\times10^3$ cells/well, followed by cultivation in an incubator (37° C., 5% $CO_2$) for 24 hours.

Thereafter, each of the cell cultures of the experimental group and the control group was replaced with 100 μL of a fresh FDPCGM. Subsequently, the cell culture of the experimental group was treated with a suitable amount of the exosome suspension prepared in section 1 of "Materials" of Example 4, so that the cell culture had a final exosome concentration of 70 μg/mL. In addition, the cell culture of the control group received no treatment.

Each group was cultivated in an incubator (37° C., 5% $CO_2$) for 96 hours. Next, each of the cell cultures of the experimental group and the control group was replaced with a growth medium containing 20% MTS solution (CellTiter 96® AQueous One Solution Cell Proliferation Assay Kit) (Promega Corporation, Cat. No. G3581), followed by cultivation in an incubator (37° C., 5% $CO_2$) for 2 hours. The respective resultant cell culture was subjected to determination of absorbance at a wavelength of 490 nm ($OD_{490}$) by a VersaMax ELISA reader (Molecular Devices). The cell viability rate (%) was calculated using the Equation (II) as described above.

The data thus obtained were analyzed according to the method described in section 1 of "General Procedures".

Figure 8:
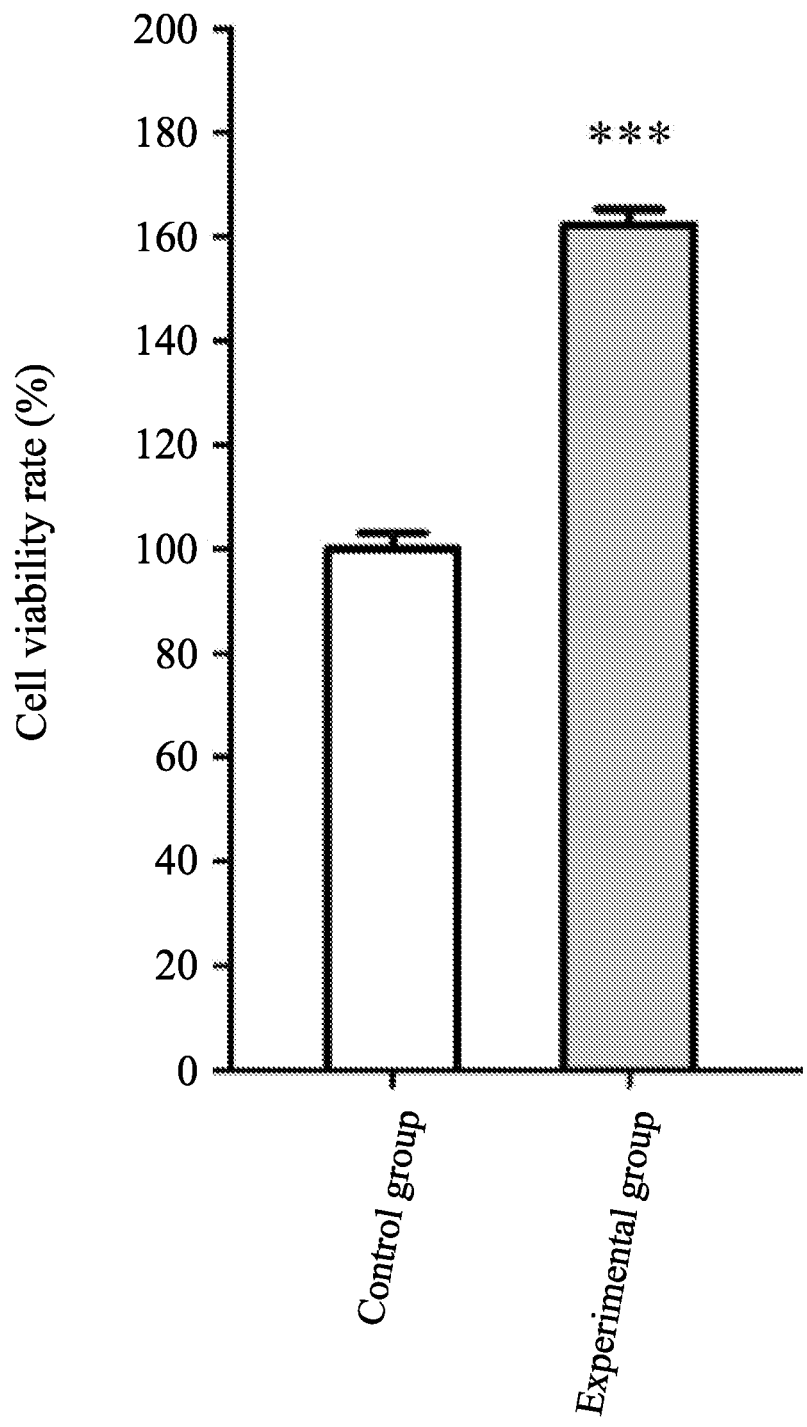
FIG. 8 shows the cell viability rate in each group of Example 7, infra, in which the symbol "***" represents $p<0.001$ (compared with the control group)

Results:

Referring to FIG. 8, the cell viability rate determined in the experimental group was significantly higher than that determined in the control group. This result indicates that the exosomes produced by the method of the present disclosure can effectively promote hair follicle regeneration, and hence can exhibit an excellent effect in improving hair loss.

Example 8. Evaluation of Anti-Inflammatory Effect of Exosome According to this Disclosure Methods:

The HSFs prepared in section 3 of "General Experimental Materials" were divided into 3 groups, including one normal control group, one experimental group, and one pathological control group. Each group of the HSFs was incubated in a respective well of 6-well culture plates containing 2 mL of DMEM supplemented with 10% FBS at $1 \times 10^5$ cells/well, followed by cultivation in an incubator (37° C., 5% $CO_2$) for 24 hours.

Thereafter, the cell culture of the experimental group was replaced with 1 mL of a fresh DMEM medium containing 0.25% CS-FBS and 1 µg/mL lipopolysaccharide (LPS) (which was obtained from *Escherichia Coli* serotype O111:B4 (Sigma)), the cell culture of the pathological control group was replaced with 1 mL of a fresh DMEM medium containing 1 µg/mL LPS, and the cell culture of the normal control group was replaced with 1 mL of a fresh DMEM medium. Subsequently, the cell culture of the experimental group was treated with a suitable amount of the exosome suspension prepared in section 1 of "Materials" of Example 4, so that the cell culture had a final exosome concentration of 0.07 µg/mL. In addition, the cell cultures of the normal control group and pathological control group received no treatment.

Each group was cultivated in an incubator (37° C., 5% $CO_2$) for 6 hours. After centrifugation at 5,000 rpm for 5 minutes, the resultant cell pellet was collected, and was then subjected to total RNA extraction and RT-PCR according to the procedures described in Example 4.

The thus obtained cDNA, serving as a DNA template, was subjected to quantitative real-time PCR according to the procedures described in Example 4 using designed primer pairs specific for IL-6 gene, IL-1β gene, and TNF-α gene shown in Table 5 and the reaction conditions shown in Table 4. 18S rRNA gene was used as an endogenous control in the quantitative analysis of real-time PCR to normalize the gene expression data.

TABLE 5

| Target gene | Primer | Nucleotide sequence (5'→3') | Size of PCR product (bp) |
|---|---|---|---|
| IL-6 gene (NCBI accession no. M54894.1) | Forward primer IL-6-F | accccaggagaagattcca (SEQ ID NO: 9) | 103 |
| | Reverse primer IL-6-R | gatgccgtcgaggatgtacc (SEQ ID NO: 10) | |
| IL-1β gene (NCBI accession no. NM_000576.2) | Forward primer IL-1β-F | gcagccatggcagaagtacc (SEQ ID NO: 11) | 70 |
| | Reverse primer IL-1β-R | agtcatcctcattgccactgtaat (SEQ ID NO: 12) | |
| TNF-α gene (NCBI accession no. NM_000594.3) | Forward primer TNF-α-F | tagcccatgttgtagcaaaccc (SEQ ID NO: 13) | 100 |
| | Reverse primer TNF-α-R | ttatctctcagctccacgcca (SEQ ID NO: 14) | |

The resultant PCR product was subjected to determination of fluorescence intensity, followed by calculating the cycle threshold (Ct) value of each of IL-6 gene, IL-1β gene, and TNF-α gene. Quantitative real-time PCR data were analyzed using the comparative Ct method as described in Example 4, and the relative mRNA expression level of each of IL-6 gene, IL-1β gene, and TNF-α gene was further calculated using the following Equation (III):

$$G = H/I \tag{III}$$

where
G=relative mRNA expression level of IL-6 gene, IL-1β gene, or TNF-α gene
H=normalized ct value of IL-6 gene, IL-1β gene, or INF-α gene in respective group
I=normalized ct value of IL-6 gene, IL-1β gene, or INF-α gene in normal control group The data thus obtained were analyzed according to the method described in section 1 of "General Procedures".

Figure 9:
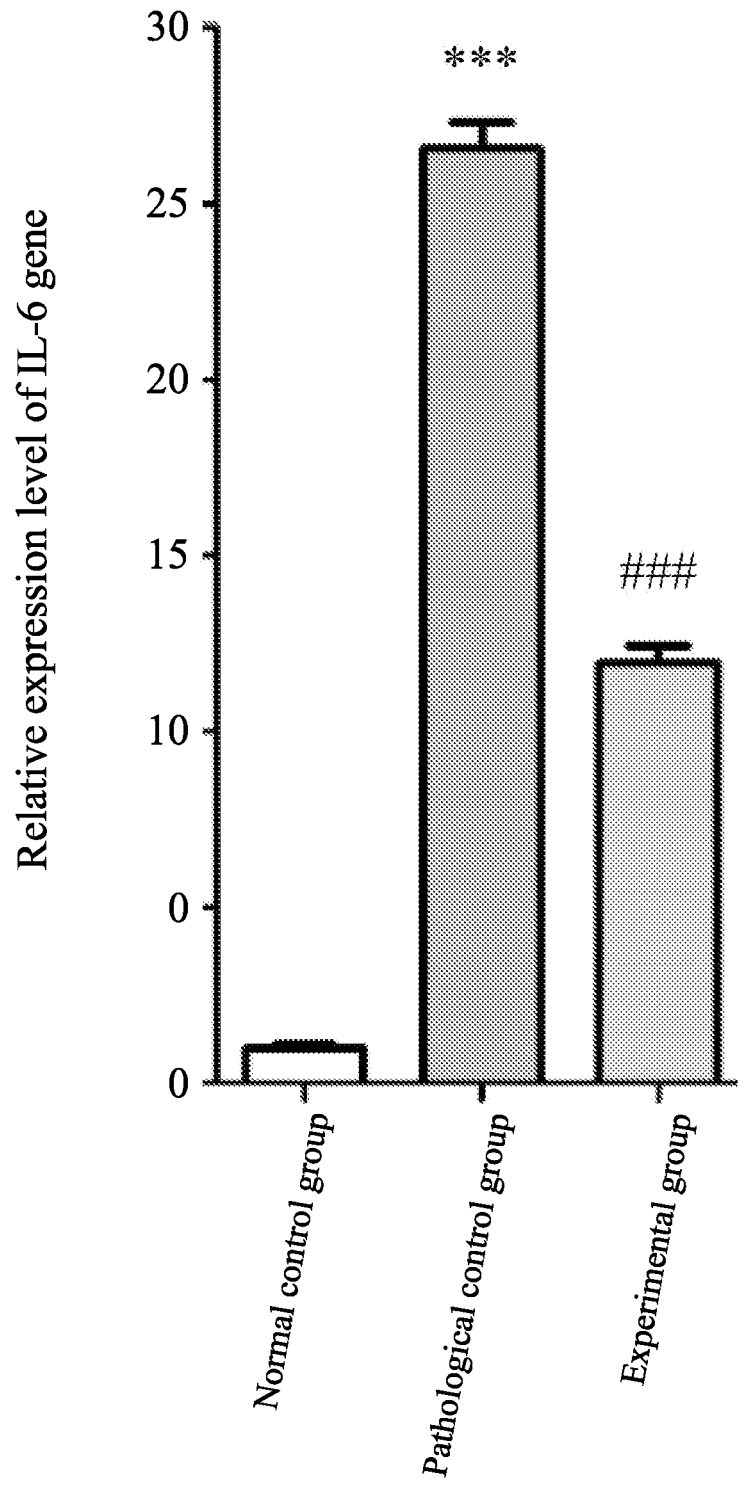
FIG. 9 shows the relative expression level of IL-6 gene in each group of Example 8, infra, in which the symbol "***" represents $p<0.001$ (compared with the normal control group), and the symbol "###" represents $p<0.001$ (compared with the pathological control group)
Figure 10:
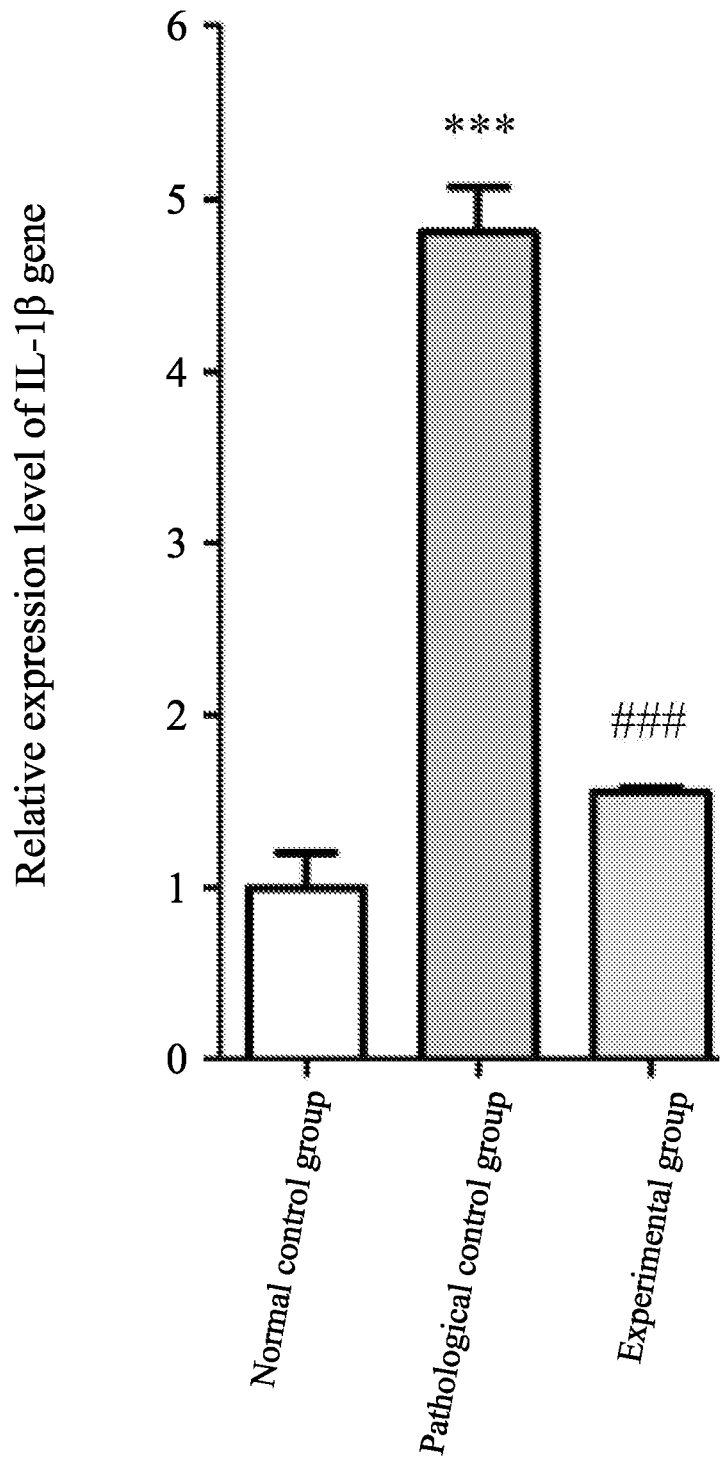
FIG. 10 shows the relative expression level of IL-1β gene in each group of Example 8, infra, in which the symbol "*" represents $p<0.001$ (compared with the normal control group), and the symbol "###" represents $p<0.001$ (compared with the pathological control group)
Figure 11:
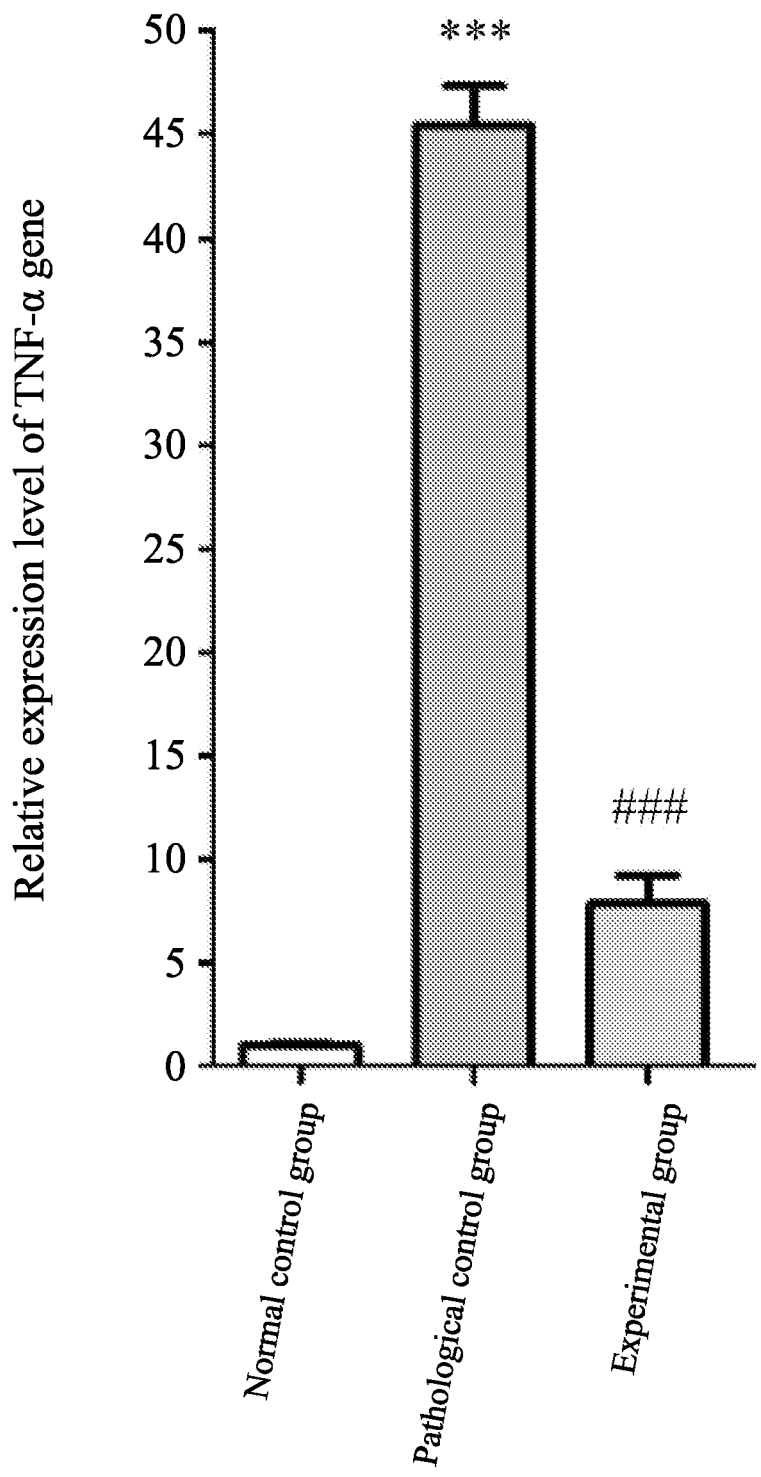
FIG. 11 shows the relative expression level of TNF-α gene in each group of Example 8, infra, in which the symbol "*" represents $p<0.001$ (compared with the normal control group), and the symbol "###" represents $p<0.001$ (compared with the pathological control group).

Results:

Referring to FIGS. 9 to 11, the relative mRNA expression levels of IL-6 gene, IL-1β gene, and INF-α gene determined in the pathological control group were significantly higher than those determined in the normal control group, indicating that LPS successfully induced inflammation in the HSFs. Moreover, the relative mRNA expression levels of IL-6 gene, IL-1β gene, and INF-α gene determined in the experimental group were significantly lower than those determined in the pathological control group.

These results indicate that the exosomes produced by the method of the present disclosure can effectively inhibit the expression of pro-inflammatory cytokines, and hence can exhibit an excellent anti-inflammatory effect.

Summarizing the above test results, it is clear that the method of the present disclosure can promote AMSCs to produce large amounts of exosomes containing high concentrations of protein and RNA. In addition, the exosome produced by the method of the present disclosure is capable of promoting skin regeneration and wound healing, reducing wrinkles and skin inflammation, and improving hair loss. Therefore, the exosome produced by the method of the present disclosure is believed to have a high potential to be developed as medicaments for skin conditions and skin care products.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for producing exosomes, comprising:
cultivating avian embryo-derived mesenchymal stem cells (AMSCs) in a culture medium containing 2,3,4',5-tetrahydroxystilbene-2-O-β-D-glucoside (THSG) at a concentration ranging from 0.1 µM to 50 µM, so as to obtain a cell culture of AMSCs; and
subjecting the cell culture of AMSCs to a separation treatment, so as to obtain the exosomes.

2. The method as claimed in claim 1, wherein the cultivation of the AMSCs is performed for a time period ranging from 24 hours to 96 hours.

3. The method as claimed in claim 1, wherein the separation treatment is selected from the group consisting of size-selective separation.

4. The method as claimed in claim 3, wherein the separation is a combination of tangential flow filtration (TFF) and size-exclusion chromatography (SEC).

5. An exosome, which is produced by a method according to claim 1, wherein the exosome has a particle size ranging from 50 nm to 200 nm, and the exosome contains higher concentrations of protein and RNA related to improving a skin condition as compared with a natural exosome derived from the AMSCs received no treatment.

6. The exosome as claimed in claim 5, which has an average particle size ranging from 50 nm to 100 nm.

7. A method for improving a skin condition, comprising administering to a subject in need thereof a composition containing an exosome as in claim 5.

8. The method as claimed in claim 7, wherein the skin condition is at least one selected from the group consisting of wound, skin aging, hair loss, and skin inflammation.

9. The method as claimed in claim 7, wherein the composition is formulated as a pharmaceutical composition.

10. The method as claimed in claim 9, wherein the pharmaceutical composition is administered by a route of oral administration or parenteral administration.

11. The method as claimed in claim 7, wherein the composition is a cosmeceutical composition.

* * * * *

SEQUENCE LISTING

<160> NUMBER OF SEQ ID NOS: 14

<210> SEQ ID NO 1

```
<211> LENGTH: 16
<212> TYPE: DNA
<213> ORGANISM: Artificial Sequence
<220> FEATURE:
<223> OTHER INFORMATION: Forward primer COL1A1-F of COL1A1 gene for
      quantitative real-time PCR

<400> SEQUENCE: 1
gtcagatggg cccccg                                                     16

<210> SEQ ID NO 2
<211> LENGTH: 20
<212> TYPE: DNA
<213> ORGANISM: Artificial Sequence
<220> FEATURE:
<223> OTHER INFORMATION: Reverse primer COL1A1-R of COL1A1 gene for
      quantitative real-time PCR

<400> SEQUENCE: 2
caccatcatt tccacgagca                                                 20

<210> SEQ ID NO 3
<211> LENGTH: 21
<212> TYPE: DNA
<213> ORGANISM: Artificial Sequence
<220> FEATURE:
<223> OTHER INFORMATION: Forward primer COL3A1-F of COL3A1 gene for
      quantitative real-time PCR

<400> SEQUENCE: 3
gaggatggtt gcacgaaaca c                                               21

<210> SEQ ID NO 4
<211> LENGTH: 21
<212> TYPE: DNA
<213> ORGANISM: Artificial Sequence
<220> FEATURE:
<223> OTHER INFORMATION: Reverse primer COL3A1-R of COL3A1 gene for
      quantitative real-time PCR

<400> SEQUENCE: 4
cagccttgcg tgttcgatat t                                               21

<210> SEQ ID NO 5
<211> LENGTH: 18
<212> TYPE: DNA
<213> ORGANISM: Artificial Sequence
<220> FEATURE:
<223> OTHER INFORMATION: Forward primer ELN-F of ELN gene for
      quantitative real-time PCR

<400> SEQUENCE: 5
caggtgcggt ggttcctc                                                   18

<210> SEQ ID NO 6
<211> LENGTH: 20
<212> TYPE: DNA
<213> ORGANISM: Artificial Sequence
<220> FEATURE:
<223> OTHER INFORMATION: Reverse primer ELN-R of ELN gene for
      quantitative real-time PCR

<400> SEQUENCE: 6
ctgggtatac acctggcagc                                                 20

<210> SEQ ID NO 7
<211> LENGTH: 20
```

```
<212> TYPE: DNA
<213> ORGANISM: Artificial Sequence
<220> FEATURE:
<223> OTHER INFORMATION: Forward primer 18s-F of 18s rRNA gene for
      quantitative real-time PCR

<400> SEQUENCE: 7
gtaacccgtt gaaccccatt                                             20

<210> SEQ ID NO 8
<211> LENGTH: 20
<212> TYPE: DNA
<213> ORGANISM: Artificial Sequence
<220> FEATURE:
<223> OTHER INFORMATION: Reverse primer 18s-R of 18s rRNA gene for
      quantitative real-time PCR

<400> SEQUENCE: 8
ccatccaatc ggtagtagcg                                             20

<210> SEQ ID NO 9
<211> LENGTH: 20
<212> TYPE: DNA
<213> ORGANISM: Artificial Sequence
<220> FEATURE:
<223> OTHER INFORMATION: Forward primer IL-6-F of IL-6 gene for
      quantitative real-time PCR

<400> SEQUENCE: 9
acccccagga gaagattcca                                             20

<210> SEQ ID NO 10
<211> LENGTH: 20
<212> TYPE: DNA
<213> ORGANISM: Artificial Sequence
<220> FEATURE:
<223> OTHER INFORMATION: Reverse primer IL-6-R of IL-6 gene for
      quantitative real-time PCR

<400> SEQUENCE: 10
gatgccgtcg aggatgtacc                                             20

<210> SEQ ID NO 11
<211> LENGTH: 20
<212> TYPE: DNA
<213> ORGANISM: Artificial Sequence
<220> FEATURE:
<223> OTHER INFORMATION: Forward primer IL-1beta-F of IL-1beta gene for
      quantitative real-time PCR

<400> SEQUENCE: 11
gcagccatgg cagaagtacc                                             20

<210> SEQ ID NO 12
<211> LENGTH: 24
<212> TYPE: DNA
<213> ORGANISM: Artificial Sequence
<220> FEATURE:
<223> OTHER INFORMATION: Reverse primer IL-1beta-R of IL-1beta gene for
      quantitative real-time PCR

<400> SEQUENCE: 12
agtcatcctc attgccactg taat                                        24

<210> SEQ ID NO 13
<211> LENGTH: 22
<212> TYPE: DNA
```

```
<213> ORGANISM: Artificial Sequence
<220> FEATURE:
<223> OTHER INFORMATION: Forward primer TNF-alpha-F of TNF-alpha gene
      for quantitative real-time PCR

<400> SEQUENCE: 13
tagcccatgt tgtagcaaac cc                                             22

<210> SEQ ID NO 14
<211> LENGTH: 21
<212> TYPE: DNA
<213> ORGANISM: Artificial Sequence
<220> FEATURE:
<223> OTHER INFORMATION: Reverse primer TNF-alpha-R of TNF-alpha gene
      for quantitative real-time PCR

<400> SEQUENCE: 14
ttatctctca gctccacgcc a                                              21
```